United States Patent [19]

Ricciardi et al.

[11] Patent Number: 4,562,155
[45] Date of Patent: Dec. 31, 1985

[54] HYBRID VIRAL PLASMID AND MICROORGANISMS CONTAINING SAME

[75] Inventors: Robert P. Ricciardi, Philadelphia, Pa.; Giuseppe Barbanti-Brodano, Bologna; Gabriele Milanesi, Pavia, both of Italy

[73] Assignee: The Wistar Institute of Anatomy and Biology, Philadelphia, Pa.

[21] Appl. No.: 496,000

[22] Filed: May 19, 1983

[51] Int. Cl.[4] ............... C12N 15/00; C12N 5/00; C12N 1/20; C12N 1/00
[52] U.S. Cl. ............... 435/172.3; 435/240; 435/253; 435/317; 935/24; 935/29; 935/32
[58] Field of Search ............... 435/172, 91, 253, 240, 435/317, 172.3

[56] References Cited

PUBLICATIONS

Binetruy et al., Eukaryotic Viral Vectors, Cold Spring Harbor Laboratory, pp. 87–92, (1982).
Kareh et al., Somstic Cell Genetics, Plenum Press, pp. 111–125, (1981).
De Pamphilis et al., Organization and Replication of Viral DNA, CRC Press Inc., pp. 37–114, (1982).
DiMaio et al., PNAS, vol. 79, pp. 4030–4034, Jul. 1982.
Gething et al., Nature, vol. 293, pp. 620–625, Oct. 1981.
Gruss et al., PNAS, vol. 78, pp. 133–137, Jan. 1981.
Lusky et al., Nature, vol. 293, pp. 79–81, (1981).
Bolivar et al., Gene 2, pp. 95–113, (1977).
Gardner et al., vol. 1, pp. 1253–1257, (1971).
McKnight et al., Carnegie Institute Year Book, vol. 78, pp. 56–61, (1978).

Primary Examiner—Alvin E. Tanenholtz
Attorney, Agent, or Firm—Howson and Howson

[57] ABSTRACT pML BK is a hybrid plasmid which is constructed of :pML which contains the entire nucleotide sequence of the plasmid pBR322 except for deletion of nucleotide sequences 1120–2490 bp and 0 to 375 bp, and BK which contains the entire nucleotide sequence of the Gardner strain of BK virus except for deletion of nucleotide sequences between bp 5089–5196. Into the pML BK plasmid may be inserted a viral or human gene X to be expressed, an example of which is TK which represents the Bam HI generated 3,600 bp DNA fragment of herpes simplex virus type 1 which contains the herpes simplex virus type 1 TK DNA. The majority of the pML BK X DNA molecules remain in the episomal or free state in the human cells 143B and express the gene X.

23 Claims, 3 Drawing Figures

HYBRID VIRAL PLASMID AND MICROORGANISMS CONTAINING SAME

DESCRIPTION

SUMMARY OF THE INVENTION

The invention relates to plasmid vectors, to the production thereof, and to the use thereof. More particularly, the invention relates to plasmid vectors adapted to receive and transcribe inserted DNA fragments.

BACKGROUND OF THE INVENTION

The development of plasmid vectors useful for recombinant DNA genetics among microorganisms is well known. The prior art efforts involving recombinant gentic manipulation of plasmids for expressing various genes have centered on *Escherichia coli* (*E. coli*) as the host organism. However, there are certain limitations regardng such use of *E. coli* and, thus it would be desirable to be able to use host microorganisms other than *E. coli*, as for example human cell lines, in recombinant gentic manipulations.

BRIEF SUMMARY OF THE INVENTION

This invention relates to novel hybrid plasmids in the nature of satellite molecules which replicate in human cells at high copy number. These hybrid plasmids persist in human cells and express exogenous viral or human genes which can serve as selectable elements to isolate those human cells which contain the expressed gene. Advantageously the plasmids can be shuttled back and forth between bacteria and human cells.

Broadly, the plasmids are virus hybrids constructed from the DNAs of the plasmid pML and the papovavirus BK, and include a further DNA insert in the nature of a viral or human gene that is to be expressed.

REFERENCE TO THE DRAWINGS

The invention will be better understood with reference to the following drawings in which:

FIG. 1 is a schematic illustration of a restriction enzyme map of the hybrid plasmid pML BK, FIG. 2 is a similar illustration of a restriction map of the hybrid plasmid pML BK TK; and FIG. 3 is a further restriction map for the generic hybrid plasmid pML, BK X, in which X is the gene to be expressed.

DETAILED DESCRIPTION OF THE INVENTION

The plasmid hybrid, pML BK, is constructed from the DNAs of the plasmid pML and the papovavirus BK.

The plasmid pML is a derivative of the well known plasmid pBR322 which consists of 4,361 base pairs (bp) and can be obtained from *E. coli* RRI, NRRLB-12014. This plasmid was isolated by Lusky, M. and Botchan M., *Nature* 293, 79–81 (1981) and is identical to pBR322 except for deletion of nucleotide bp 1120–2490 and 0 to 375 bp. The pML plasmid is 2,991 bp and retains the ampicillin resistance gene but not the tetracycline resistance gene of pBR322.

The Gardner strain of BK papovavirus can be obtained from the cell line ATCC VR837. The prototype Gardner strain has a genomic length of 5,196 bp and when digested with endonucleases Eco RI and Bam HI, yields a fragment 5,089 bp in length. This 5,089 bp fragment, which is used in the construction of pML BK and pML BK X, where X is a viral or human gene inserted into the plasmid, only deletes the nucleotide sequences required for expression of late viral proteins and thus yields the viral DNA incapable of infection.

The construction of the hybrid plasmid pML BK is as follows: (1) the DNA of the BK virus is digested with both Eco RI and Bam HI yielding a linear 5,089 bp DNA fragment. (2) the DNA of pML is similarly digested with Eco RI and Bam HI to yield a linear 2,616 bp fragment. These fragments are isolated and joined together using a T4 DNA ligase using established techniques of recombinant DNA technology which are referred in the laboratory manual, *Molecular Cloning,* Maniatis, T., Fritsch, E. F. and Sambrook, J., Cold Spring Harbor, 1982, incorporated herein by reference. By this procedure the plasmid virus hybrid is produced such that the DNA from each is joined together at one end at the Eco RI sites and at the other end by the BAM HI sites.

Figure 3:
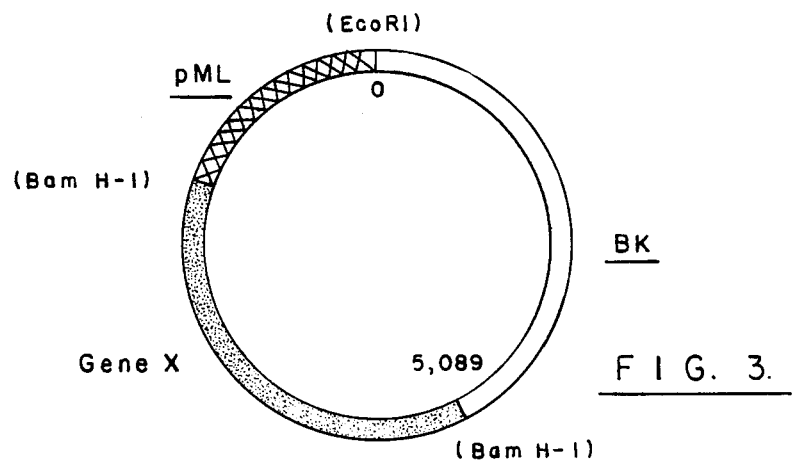

Referring to the restriction map for the hybrid plasmid pML BK, the restriction enzyme sites Eco RI and Bam HI are shown in parentheses. The entire circular molecule is 7,705 bp in length. The Eco RI site designated zero (0) to the Bam HI site 5,089 contains BK viral sequences (clear). The pML sequences extend from bp 5,089 to 7,705 (cross hatched). The Eco RI site and Bam HI site are convenient cloning sites for the insertion of additional genes (see e.g. viral or human gene X in FIG. 3).

Figure 1:
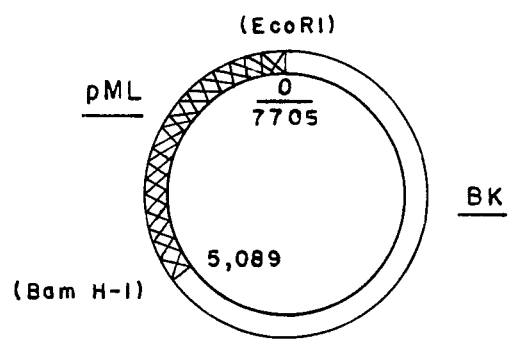
Figure 2:
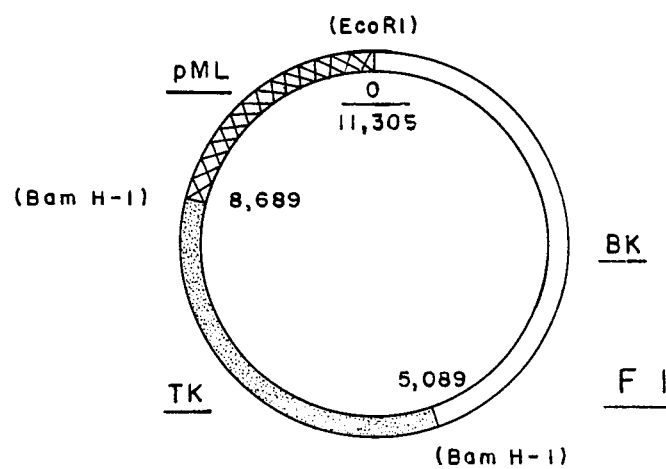

The procedure for insertion of an additional gene, viral or human, into the hybrid plasmid pML BK involves digesting the plasmid with Bam HI and ligating a Bam HI DNA fragment containing the desired gene to the Bam HI site by standard recombinant DNA cloning procedures. Thus, in this manner the 3,600 bp Bam HI DNA fragment containing the herpes simplex virus type I TK gene may be inserted into the plasmid pML BK to form the plasmid pML BK TK. The TK gene can be obtained from the recombinant DNA clone, pHSV106, described by McKnight, S. L., Croce, C., and Kingsbury, R., Carnegie Institute of Washington Year Book 78, 56–61 (1979). This TK gene can also be isolated as the 3,600 bp DNA fragment from the herpes simplex virus type I after digestion with the restriction endonuclease Bam HI (Pellicer, A., Wigler, M., Axel, R., and Silverstein, S., *Cell* 14, 133–141 (1978). Herpes simplex virus type I can be obtained from the American Type Culture Collection, Accession number ATCC VR733. The restriction map of the recombinant DNA molecule or plasmid pML BK TK is illustrated in FIG. 2. The restriction enzyme sites Eco RI an Bam HI, as in FIG. 1, are shown in parentheses. The entire circular molecule is 11,305 bp in length. The Eco RI site, designated zero (0) to Bam HI site 5,089 contains the BK viral sequence (clear). The herpes TK sequences extend from bp 5,089 to 8,689 (stippled) and the pML sequence extends from bp 8,689 to 11,305 (cross hatched). As with the hybrid plasmid pML BK, the Eco RI site and Bam HI site are convenient cloning sites for the insertion of additional genes.

In both the plasmids pML BK and pML BK TK, the pML sequences permit amplification of the plasmids to occur in bacteria such that milligram quantities of the plasmids are obtained. The BK DNA sequences permit replication of the plasmids to occur in the human cell line 143B (ATCC CRL 8303), and also allows the plasmids to remain in the episonal state in such cell line. The TK gene of the hybrid plasmid pML BK TK produces the enzyme TK in the 143B cell line in which de novo synthesis of DNA has been blocked by hypoxanthine aminopterin thymidine (HAT) medium. The cells which produce TK from the TK gene of the pML BK TK molecule permit DNA synthesis to occur by salvage pathway mechanisms of purine, pyrimidine metabolism.

Thus, the plasmid pML BK X (FIG. 3), where X can be TK, EIA Ad 5 (Example 8, infra), or some other inserted viral or human gene, serves as a shuttle vector that replicates in both bacteria and human cells, is able to persist in the episomal or free state, and is able to express the X gene in human cells.

The insert gene X can be viral, such as any member of the herpes family of viruses, adenovirus, cytomegalovirus, vaccina virus, and the like, or human genes which express protein products.

Thus, the hybrid plasmid pML BK X (FIG. 3) is useful as a cloning vector in DNA work wherein desired genes are incorporated into the hybrid plasmid, and the resulting plasmid then transforms into a suitable host, such as the human cell line 143B. Accordingly, the plasmids can be useful in the production of vaccines.

The following examples are illustrative of the process and products of subject invention but are not to be construed as limiting. All percentages are by weight and all solvent mixture proportions are by volume unless otherwise noted.

The following microorganisms and viruses are available from the Americal Type Culture Collection, Rockville, Md., United States.
ATCC VR837—BK virus (Garnder Strain)
ATCC VR733—Herpes simplex virus type I (Strain F)
ATCC VR5—Human Adenovirus type 5
The following bacteria are available from the Northern Regional Research Laboratory, U.S. Department of Agriculture, Peoria, Ill., United States.
NRRL B-11371—*E. coli* HB 101
The following human tissue culture cells were deposited with the Institute for Medical Research, Camden, N.J., United States on July 19, 1982, accession number GM 5887, and with the American Type Culture Collection on May 17, 1983.
143B Human Tissue TK Minus Cells (ATCC CRL 8303)

EXAMPLE 1

Isolation of the vector plasmid pML DNA from *E. coli* HB101 NRRL B-11371

A culture of *E. coli* HB101 NRRL B-11371 containing the pML plasmid DNA is grown overnight in L-broth containing the following ingredients:
Bacto tryptone (Difco)—10 g/liter
Bacto yeast extract (Difco)—5 g/liter
NaCl—10 g/liter
Ampicillin—100 mg/liter The following day, 5 ml of the overnight is used to inoculate 0.5 liter of L-broth. The cells are grown to an optical density of 0.4 at a wavelength of 600 nm at which time chloramphenicol (Sigma) is added to the 1-liter culture to give a final concentration of 0.17 mg/ml. The culture is shaken for 12-16 hours at 37° C. The bacteria are collected by centrifugation at 9,000 rpm for 10 minutes at 5°-20° C. The bacteria pellet is resuspended in 5 ml of glucose buffer (glucose buffer: 0.9% glucose; 0.025M Tris, pH 8.0; 10 mM ethylenediaminetetraacetic acid (EDTA)) and 50 mg lysozyme (Sigma). The lysate is held at R.T. for 10 minutes and then 20 ml of sodium dodecyl sulfate (SDS)/NaOH solution (0.2N NaOH; 0.05% SDS (Sigma)) is added. The mixture is placed into an ice bath and 15 ml of cold 5M acetate solution is added. After 10 minutes, the mixture is centrifuged at 10,000 rpm at 4° C. The supernatant is collected and the DNA of the supernatant is precipitated with 0.6 volumes of isopropanol at room temperature.

After 10 minutes the DNA is pelleted at 10,000 rpm for 10 minutes at 5° C. The pellet is washed with 70% ethanol, dried, and resuspended in 0.01M Tris pH 8.0, 0.01M EDTA and 30 mM NaCl and added to 9 g of CsCl in a final volume of 11 ml containing 5 mg of ethidium bromide. This solution is spun in a centrifuge at 47,000 rpm for 24 hours at 15° C. and the lowest band in the centrifuge tube visualized by an ultra violet (U.V.) (280 nm) lamp is collected with a hypodermic syringe. The collected DNA/CsCl is diluted with 3 volumes of water and adjusted to a final concentration of 0.2M Na acetate and the DNA is precipitated with 3 volumes of water at −20° C. overnight. The plasmid DNA is finally collected by centrifugation at 10,000 rpm for 20 minutes at 5° C., dried under vacuum and resuspended in 10 mM Tris, pH 8.0 and 1 mM EDTA.

EXAMPLE 2

Isolatin of BK DNA.

The BK viral DNA is obtained from BK virus (ATCC VR837). The viral DNA is extracted from purified virions by the procedure of Meneguzzi et al., *J. of Virol.* 25, 940-943, 1978. Essentially, the virion suspension is heated at 50° C. for 30 minutes in 10 mM Tris HCl pH 7.5; 10 mM EDTA and 0.5% SDS and 50 μg of proteinase k (Sigma) per ml. The incubation temperature is then increased to 37° C. for 3 hours. Ethidium bromide (400 μg/ml of original solution) and CsCl (1.6 μg/cm$^3$ final density) are added. The material is centrifuged for 50 hours at 43,000 rpm at 10° C. and the superhelical band of BK virus DNA is collected and extracted with isopropanol and dialyzed against 10 mM Tris, pH 7.5 and 1 mM EDTA.

EXAMPLE 3

Isolation of the TK gene of Herpes Simplex Virus Type 1.

Herpes simplex virus type 1 TK DNA is obained from a recombinant DNA molecule pH SV106 described by McKnight S. L., Croce, C. and Kingsbury, R., Carnegie Institute of Washington Year Book 78, 56–61, 1979, and constitutes the 3,600-bp Bam HI fragment of herpes simplex virus type 1 DNA. Essentially, the pH SV106 plasmid is digested with Bam HI to remove the 3,600-bp fragment containing the herpes simplex virus type 1 DNA which is then isolated by fractionation and elution from an agarose gel by established recombinant DNA cloning procedures (*Molecular Cloning*, supra). This same Bam HI fragment can be isolated from herpes simplex virus type 1 obtainable from ATCC-VR733 (strain F) by the procedures outlined by Pellicer et al., *Cell* 14, 133–141, 1978.

EXAMPLE 4

Preparation of the hybrid virus plasmid pML BK

The pML plasmid and BK viral DNAs are each digested with both Eco RI and Bam HI restriction endonucleases. The 5,089 bp Bam HI/Eco RI fragment of BK is ligated to the 2,616 bp fragment of pML (which contains an ampicillin resistence gene) using T4 DNA ligase by established procedures described in *Molecular Cloning*, supra. This ligated DNA is transfected into the HB101 strain of *E. coli* NRRL B-11371 using established procedures outlined in *Molecular Cloning*, supra. The ampicillin-resistant *E. coli* are screened by established procedures of recombinant DNA technology (*Molecular Cloning*, supra.) such that the HB101 *E. coli* which contain the pML BK DNA (7,705 bp in length) are isolated and the DNA of pML BK is purified as described in Example 1.

EXAMPLE 5

The preparation of the hybrid plasmid pML BK TK.

The pML BK DNA is digested with Bam HI to linearize the DNA and is directly treated with bacterial alkaline phosphatase (PL Biochemicals) in 10 mM Tris, pH 8.0 at 65° C. for 60 minutes. The pML BK DNA is phenol extracted 1X and further extracted 2X with chloroform: isoamyl alcohol (24:1). This pML BK DNA is then ligated to the 3,600 Bam HI fragment of herpes simplex virus type 1 DNA containing the thymidine kinase gene (described above in Example 3). The ligated DNA is transfected into *E. coli* HB101 NRRL B-11371 and the ampicillin-resistant colonies are screened for those which contain the 11,305 bp pML BK TK molecule by procedures described in Example 4 above. Isolation of pML BK TK is as described in Example 1.

EXAMPLE 6

Introduction of pML BK TK DNA into the human tissue culture cell 143B (ATCC CRL 8303)

pML BK TK DNA (120 micrograms) is precipitated in 70% ethanol 0.2M Na acetate, pH 5.5 final concentration at $-20°$ C. overnight in a sealed 1.5 ml Eppendorf tube. The DNA is pelleted at $10,000 \times g$ in an Eppendorf microfuge for 10 minutes. All operations from here on are performed in a sterile tissue culture hood and essentially according to procedure of Graham and Van der Eb, *Virology* 52, 456–467, 1973. The outside of the tube is rinsed with 70% ethanol and then the ethanol supernatant is poured off. The pML BK TK DNA is allowed to air dry and is then dissolved in 2.62 ml of 1 mM Tris, pH 7.9; 0.1 mM EDTA. Then 375 $\mu$l of 2M $CaCl_2$ is added to the dissolved DNA. A 3.0 ml solution of HBS buffer (280 nM NaCl, 50 mM Hepes buffer (N-2-hydroxyethylpiperazine-N'-2-ethanesulfonic acid) (Sigma) pH 7.1 and 1.5 mM $Na_3PO_4$) is slowly added to the solution containing pML BK TK DNA while simultaneously introducing a steady stream of air bubbles to assure even mixing. The DNA-calcium-phosphate solution is allowed to stand at room temperature for 30 minutes and then 1.0 ml is added to each of 6 T-75 cm$^2$ tissue culture flask (Falcon) containing approximately $9 \times 10^6$ 143B TK minus human cells (Croce, C. M., J. Barrick, A. Linnenbach, H. Koprowski, *J. Cell Physilogy* 99, 279–286, 1979) which are fed 9.0 ml of minimal essential medium (MEM) (Eagle, H., *Science* 130, 432, 1959; available from GIBCO) 4 hours prior to the addition of DNA. The cells are incubated in a 37° C. incubator (5% $CO_2$) 5–7 hours. The MEM medium containing the DNA is removed by aspiration and 25 ml of fresh medium is supplied to the cells. Following a 20–24 hour incubation period, the cells are split using versene buffer (GIBCO) at a ratio of 1:2 and distributed into 100 mM petri dishes (Falcon) in 10 ml of HAT medium (100 $\mu$M, 0.4 $\mu$M, 16 $\mu$M, respectively, hypoxanthine/aminopterine/thymidine; Littlefield, J. W., *Exp. Cell Res.* 41, 190–196, 1965). The cells are maintained at 37° C. and 5% $CO_2$ for 2–3 weeks and the HAT medium is changed every 3–4 days.

EXAMPLE 7

Isolation of 143B human cells which contain pML BK TK DNA.

The 143B TK minus cells die in HAT medium while those cells which contained TK gene survive and form small colonies on the surface of the plastic petrie plate. The surviving cell colonies are removed with versene buffer using glass cloning rings and are separately grown in HAT medium. The DNAs from these colonies are isolated by the established method of HIRT (Hirt, B., *J. Mol. Biol.* 26, 365–369, 1967) and analyzed by the well-known method of Southern blot analysis (Southern, E. M., *J. Mol. Biol.* 98, 503–517, 1975). These results demonstrate that the pML BK TK DNA persists in the 143B human cell line with the majority of the pML BK TK molecules (about 90%) remaining in the free or episomal state and by restriction enzyme analysis using Bam HI and Eco RI contain the entire pML BK TK molecule. About 10% of the pML BK TK DNA molecules contain uncharacterized deletions.

EXAMPLE 8

The pML BK TK DNA isolated from the 143B human cell can be shuttled back into bacteria.

The pML BK TK DNA from the HIRT extraction (HIRT supernatant) referred to in Example 6 is transfected in the HB101 strain of *E. coli*. The *E. coli* HB101 cells are made competent by the standard $CaCl_2$ technique (*Molecular Cloning*, supra.) and are transfected with 500 nanograms of HIRT supernatant DNA from 143B thymidine-positive cells containing pML BK TK DNA (Example 6). *E. coli* HB 101 cells which are resistant to ampicillin are isolated and grown in 10 ml overnight cultures containing LB broth an 0.1 mg/ml of ampicillin. The plasmid DNA is isolated from these bacterial colonies by the rapid lysis procedure (Holms, D. S. and Quigley, *Anal. Biochem.* 114, 193, 198) and one-half of the extracted DNA is digested with Bam HI and the other half of the sample remains undigested. Separation of these molecules on 1% agarose gels containing 0.5 $\mu$g/ml of ethidium bromide and visualization of the DNA bands on a 280-nm-UV box indicates that about 95% of the pML BK TK molecules contain the 3,600 bp herpes simplex virus type 1 TK DNA as well as the intact pML and BK DNAs in the form of the original full-length pML BK TK DNA molecule.

EXAMPLE 9

Preparation and isolation of the hybrid plasmid pML BK containing the EIA transforming genes of adenovirus type 5 (Ad 5)

The 0–76 m.u. region of the Ad 5 was obtained from Massachusetts Institute of Technology, and was contained in the Eco RI site of pBR322. In a series of digestions described below, the EIA transforming gene of adenovirus which encompasses the 0–1632 bp fragment is cloned into pML BK. Firstly, the 0–76 m.u. fragment of Ad 5 DNA in pBR322 (above) is reduced to a 0–59.5 fragment by digestion with Bam HI such that the 0 m.u. end is cloned into the Eco R1 site of pBR322 and the 59.5 m.u. end was cloned into the Bam HI site of pBR322 (molecule A). Secondly, the 0–59.5 m.u. insert is further reduced in length by digestion with Hpa I to yield a 0–4.5 m.u. segment joined to (designated by /) 57–59.5 m.u. segment, i.e. 0–4.5/57.5–59.5 m.u. (molecule B). Thirdly, molecule B is digested with Hpa I opening up the 4.5 to 57 junction and the 180 bp SMA M Fragment of Ad 2 is inserted to create a poly A addition site, i.e. an insert containing 0–4.5 m.u./SMA M/57–59.5 m.u. with the Eco RI site at 0 m.u. position and the Bam HI site a 59.5 m.u. (molecule C). The Bam HI to Eco I insert of molecule C is removed and the Eco RI to Bam HI segment of pBR322 (375 bp) is ligated to the Eco RI (0 m.u.) end of the insert to give a 3,005 bp length of DNA containing the 5' terminal Bam HI to Eco RI of pBR322/0–4.5 m.u. Ad 5/SMA M Ad 2/57–59.5 m.u. of Ad 5, terminating at the 3' end (59.5 m.u.) with a Bam HI site (molecule D). This 3,005 bp DNA (molecule D) is ligated into the Bam HI of pML BK and is referred to here as pML BK EIA Ad 5. pML BK EIA Ad 5 DNA is transfected into *E. coli* HB101 as described in Example 5, and isolation of pML BK EIA Ad 5 DNA is as described in Example 1. The Ad 5 DNA described in this example (9) may be obtained from the ATCC, accession number ATCC VR 5.

EXAMPLE 10

Expression of Ad 5 EIA genes in the 143B human cell containing pML BK EIA Ad 5.

The pML BK EIA Ad 5 DNA is introduced into the 143B cells as described in Example 6. After 60 hours, these cells are physically scraped from the tissue culture plates and cytoplasmic RNA is prepared as described by Berger and Berkenmeir, *Biochemistry* 18, 5143, 1979. The RNA is subject to S-1 nuclease analysis as described by Berk, A. J. and Sharp, P. A. *Cell* 14, 695–711, 1978. The level of EIA RNAs expressed is equivalent to the amount produced during a lytic infection of Ad 5. This example demonstrates that genes other than TK are efficiently expressed in the pML BK molecule described in Example 4.

EXAMPLE 11

Cloning other viral and human genes into pML BK.

A viral or human gene referred to here as X, which does not contain Bam HI DNA sequences at its termini, may be inserted into the Bam HI site of pML BK (Example 4) by adding Bam HI linkers available from many commercial companies (e.g. Bethesda Research Laboratories) to the termini of X. The procedures for this operation are a routine of the recombinant DNA technology and are described by Molecular Cloning, supra.

The following microorganisms are available from the permanent collection of the American Type Culture Collection, Rockville, Md., United States.

| Deposit Accession Number | Description | Date of Deposit |
|---|---|---|
| ATCC 39370 | *E. coli* HB101 (pML BK) | May 17, 1983 |
| ATCC 39369 | *E. coli* HB101 (pML BK TK) | May 17, 1983 |
| ATCC 39371 | *E. coli* HB101 (pML BK EIA Ad 5) | May 17, 1983 |
| ATCC CRL 8304 | 143B Cells (pML BK TK) | May 17, 1983 |
| ATCC CRL 8303 | 143B Cells | May 17, 1983 |

The deposits are available to the public upon grant of a patent to the assignee, The Wistar Institute of Anatomy and Biology, Philadelphia, Pa., United States, disclosing them. The above-identified deposits of microorganisms with the American Type Culture Collection will be maintained for a period of thirty years or for the enforceable life of the patent or for five years after the last request of a sample of any such deposit, whichever is longest. The deposits are also availalbe as required by foreign patent laws in countries where counterparts of this application are filed, and by Rule 9.1 of the Budapest Treaty. The availability of a deposit does not constitute a license to practice the invention of this application in derogation of any patent issued thereon or on any division or continuation of this application.

We claim:

1. *E. coli* HB101 (pML BK) having the deposit accession number ATCC 39370.

2. Hybrid plasmid pMK BK characterized as follows:
   (a) it is a hybrid plasmid which has the 2,616 by nucleotide sequence from Eco RI to Bam HI of plasmid pML and a foreign DNA insert between the Bam HI and Eco RI sites of pML;
   (b) said DNA insert being the 5,089 bp Bam HI/Eco RI fragment of BK papovavirus.

3. Essentially pure plasmid pML BK which is characterized by 7,705 bp and a restriction endonuclease cleavage map as shown in the drawing, FIG. 1.

4. A recombinant hybrid plasmid for transformation of a microbial or human cell host, said plasmid comprising the 2,616 bp nucleotide sequence from Eco RI/Bam HI of the plasmid vector pML ligated to the 5,089 bp Eco RI/Bam HI DNA fragment of the papovavirus BK into which a DNA segment which codes for a viral or human gene has been inserted.

5. The recombinant plasmid of claim 4, in which said DNA segment is selected from the group consisting of the viral genes TK, Ad 5 EIA, Ad 2 Va, Ad 5 E4, and Herpes glycoprotein D, and the human genes human α globin and human β globin.

6. The recombinant plasmid of claim 4, in which said DNA segment is inserted at the Bam HI site.

7. The recombinant plasmid of claim 4, in which said DNA segment is inserted at the Eco RI site.

8. A transformant microorganism or cell line which includes a recombinant plasmid, said plasmid comprising the 2,616 bp nucleotide sequence from Eco RI/Bam HI of the plasmid vector pML ligated to the 5,089 bp Eco RI/BAM HI DNA fragment of the papovavirus BK into which a DNA segment which codes for a viral or human gene has been inserted.

9. A transformant microorganism according to claim 8 in which said DNA segment is inserted at the Bam Hi site.

10. A transformant microorganism according to claim 8 in which said DNA segment is inserted at the Eco RI site.

11. A transformant microorganism according to claim 8 in which the microorganism is *E. coli*.

12. A transformant cell line according to claim 8 in which the cell line comprises the human cell line 143B.

13. A process for producing a viral or human gene which comprises culturing a transformant microorganism or cell line, said microorganism or cell line including a recombinant hybrid plasmid, said plasmid comprising the 2,616 bp nucleotide sequence from Eco RI to Bam HI of the plasmid vector pML ligated to the 5,089 bp Eco RI/Bam HI DNA fragement of the papovavirus BK into which a DNA segment which codes for a viral or human gene has been inserted.

14. The process according to claim 13 in which said microorganism is *E. coli*.

15. The process according to claim 13 in which said cell line comprises the human cell line 143B.

16. *E. coli* HB101 (pML BK TK) having the deposit accession number ATCC 39369.

17. TK minus human cell line (pML BK TK) having accession number ATCC CRL 8304.

18. Hybrid plasmid pML BK TK characterized as follows:
   (a) it is a hybrid plasmid which has the 2,616 bp nucleotide sequence from Eco RI to Bam HI of plasmid pML and foreign DNA inserts between the Bam HI and Eco RI sites of pML;
   (b) one said DNA insert being the 5,089 bp Bam HI/Eco RI fragment of BK papovavirus and the other DNA insert being the TK gene of herpes simplex virus type I, said TK gene being located downstream of said Bam HI/Eco RI fragment of BK papovavirus.

19. Essentially pure plasmid pML BK TK which is characterized by 11,305 bp and a restriction endonuclease cleavage map as shown in the drawing, FIG. 2.

20. Hybrid plasmid pML BK X characterized as follows:
   (a) it is a hybrid plasmid which has the 2,616 bp nucleotide sequence from Eco RI to Bam HI of plasmid pML and foreign DNA inserts between the Bam HI and Eco RI sites of pML;
   (b) one said DNA insert being the 5,089 bp Bam HI/Eco RI fragment of BK papovavirus and the other DNA insert being a viral or human gene X, said gene X being located downstream of said Bam HI/Eco RI fragment of BK papovavirus,
   (c) said plasmid being episomal and at high copy number in human cells and being capable of expressing said gene X.

21. A process for preparing hybrid plasmid pML BK which comprises:
   (a) digesting plasmid pML with Eco RI and Bam HI to obtain a linear DNA fragment of 2,616 bp;
   (b) digesting the DNA of BK papovavirus with Eco RI and Bam HI and recovering a 5,089 bp DNA fragment; and
   (c) ligating said linear plasmid DNA fragment and said BK papovavirus DNA fragment to obtain the hybrid plasmid pML BK.

22. A process for preparing a hybrid plasmid which comprises
   (a) linearizing the plasmid pML BK with Bam HI to obtain linear plasmid DNA,
   (b) digesting herpes simplex virus type I with Bam HI and recovering the 3,600 bp DNA containing the TK gene, and
   (c) ligating said linear plasmid DNA and said DNA containing the TK gene to obtain the hybrid plasmid pMK BK TK.

23. *E. coli* HB101 (pML BK EIA Ad 5) having the accession number ATCC 39371.

* * * * *